(12) United States Patent
Gorin et al.

(10) Patent No.: US 12,146,847 B2
(45) Date of Patent: Nov. 19, 2024

(54) SENSOR DEVICE, AND METHOD FOR MANUFACTURING SENSOR DEVICE

(71) Applicant: Samsung Electronics Co., Ltd., Suwon-si (KR)

(72) Inventors: Dmitry Aleksandrovich Gorin, Saratov (RU); Pavel Olegovich Kapralov, Korolev (RU); Sergei Viktorovich German, Atkarsk (RU); Timur Ikromovich Ermatov, Bolshaya Izhora (RU); Artem Yurievich Klimchuk, Tambov (RU); Vladislav Valerievich Lychagov, Saratov (RU); Polina Grigorievna Rudakovskaya, Moscow (RU); Evgeniia Yurievna Salamatova, Volgograd (RU)

(73) Assignee: Samsung Electronics Co., Ltd., Suwon-si (KR)

( * ) Notice: Subject to any disclaimer, the term of this patent is extended or adjusted under 35 U.S.C. 154(b) by 310 days.

(21) Appl. No.: 17/743,140

(22) Filed: May 12, 2022

(65) Prior Publication Data

US 2022/0268720 A1 Aug. 25, 2022

Related U.S. Application Data

(63) Continuation of application No. PCT/KR2020/019111, filed on Dec. 24, 2020.

(30) Foreign Application Priority Data

Dec. 24, 2019 (RU) .......................... RU2019143523
Oct. 16, 2020 (KR) ........................ 10-2020-0134104

(51) Int. Cl.
*G01N 27/14* (2006.01)
*G01N 27/12* (2006.01)
*G01N 33/00* (2006.01)

(52) U.S. Cl.
CPC .......... *G01N 27/125* (2013.01); *G01N 27/14* (2013.01); *G01N 33/0047* (2013.01)

(58) Field of Classification Search
CPC ... G01N 27/125; G01N 27/14; G01N 33/0047
See application file for complete search history.

(56) References Cited

U.S. PATENT DOCUMENTS 8,585,974 B2 11/2013 Chakravarty et al.
9,213,000 B2 12/2015 Ozin et al.
(Continued)

FOREIGN PATENT DOCUMENTS

DE 10 2013 208 603 A1 11/2014
EA 028768 B1 12/2017
(Continued)

*Primary Examiner* — Jamel E Williams
(74) *Attorney, Agent, or Firm* — Jefferson IP Law, LLP

(57) ABSTRACT

A sensor device configured to accurately identify a volatile compound from water vapor even at high humidity, and a method for manufacturing the sensor device are provided. The sensor device includes a measuring transducer including a pixel array on which volatile compounds and water vapor are condensed and a sensitive porous dielectric layer provided in a form of a plurality of spheres constituting the pixel array, a temperature controller provided around the pixel array, and configured to control temperature of each of pixels constituting the pixel array and temperature of the pixel array, a detection device connected to the measuring transducer, and configured to detect a response pattern of the volatile compounds through the pixel array, an analyzer configured to process, classify, and store the response pattern, a stimulating source connected to the measuring transducer, and configured to stimulate the measuring transducer, and at least one processor.

13 Claims, 13 Drawing Sheets

(56) References Cited

U.S. PATENT DOCUMENTS

| | | | |
|---|---|---|---|
| 11,037,032 B2 | 6/2021 | Abbott et al. | |
| 2019/0107502 A1 | 4/2019 | Carr | |
| 2019/0277762 A1 * | 9/2019 | Zhao | .................... G01N 21/554 |

FOREIGN PATENT DOCUMENTS

| | | | | |
|---|---|---|---|---|
| JP | 2016197016 A | * | 11/2016 | |
| KR | 10-2011-0120035 A | | 11/2011 | |
| KR | 2011120035 A | * | 11/2011 | |
| KR | 10-2015-0042311 A | | 4/2015 | |
| KR | 2015042311 A | * | 4/2015 | |
| WO | 2004/029336 A3 | | 4/2004 | |
| WO | 2007/008440 A2 | | 1/2007 | |
| WO | 2010/027854 A1 | | 3/2010 | |
| WO | 2011/121077 A1 | | 10/2011 | |
| WO | 2018/208332 A2 | | 11/2018 | |
| WO | WO-2018208332 A3 | * | 12/2018 | ......... G01N 33/5058 |

* cited by examiner

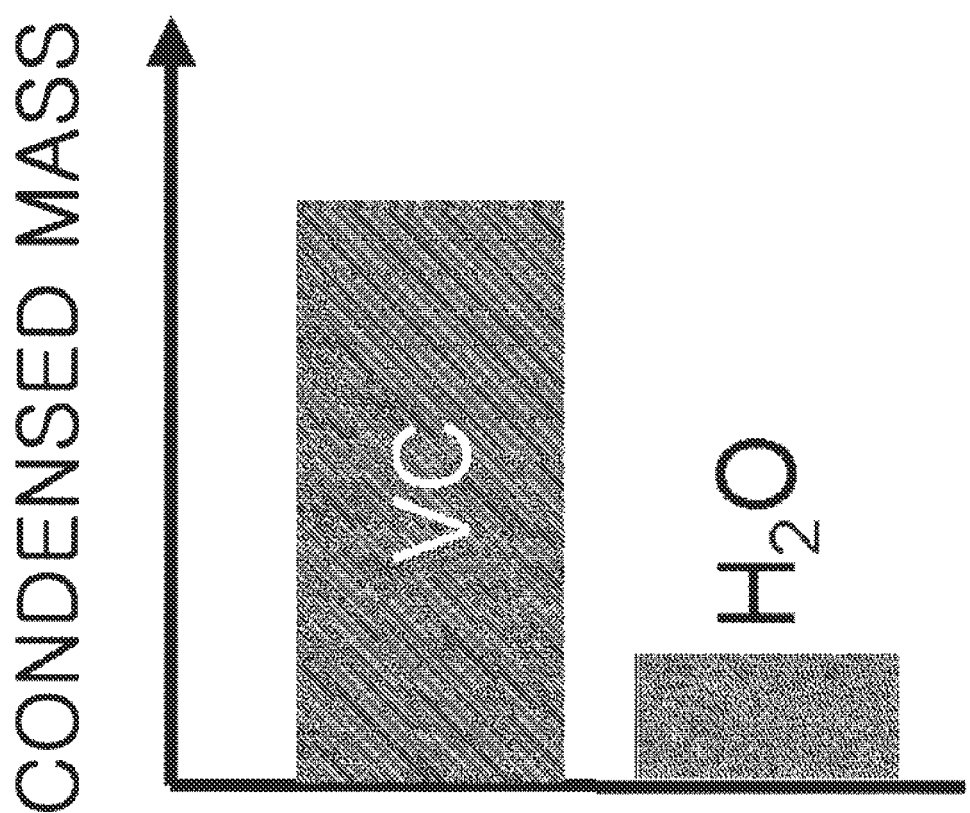

SENSOR DEVICE, AND METHOD FOR MANUFACTURING SENSOR DEVICE

CROSS-REFERENCE TO RELATED APPLICATION(S)

This application is a continuation application, claiming priority under § 365(c), of an International application No. PCT/KR2020/019111, filed on Dec. 24, 2020, which is based on and claims the benefit of a Russian patent application number 2019143523, filed on Dec. 24, 2019, in the Russian Intellectual Property Office, and of a Korean patent application number 10-2020-0134104, filed on Oct. 16, 2020, in the Korean Intellectual Property Office, the disclosure of each of which is incorporated by reference herein in its entirety.

BACKGROUND

1. Field

The disclosure relates to a volatile compound sensor device and a method for manufacturing the same. More particularly, the disclosure relates to a sensor device capable of improving the stability and life and accurately identifying a volatile compound from water vapor even at high humidity, and a method for manufacturing the sensor device.

2. Description of Related Art

A volatile compound sensor device can be used in refrigerators to detect the degrees of freshness of various products and determine the degree of readiness of products and a burnt degree of food in cooking.

Moreover, the volatile compound sensor device can be used in a perfume industry to detect a preferred smell from a finished perfume product, and used to analyze components of air discharged from personal and occupational medical devices.

One of the directions in detecting volatile compounds in recent years is generation of technical means, such as Electronic nose (e-nose) designed to detect smells based on the principle of the human's or animal's nose.

Such a device is configured with a set of receptors that are respectively sensitive to a plurality of volatile compounds, and an array of responses from all the receptors with respect to a specific smell is decided as a unique array.

Accordingly, the e-nose provides a whole array of responses that are further analyzed through a machine learning algorithm.

Meanwhile, one of main problems of the technical device, such as e-nose, is that the e-nose depends on environment conditions, and indexes of the e-nose change at different temperatures and different humidity indications, which leads to inaccuracy of obtained data.

Most of typical sensing units, such as e-nose, are highly sensitive to ambient humidity indications.

In addition, chemical sensing units have short service lives due to the decomposition of chemical components. A metal oxide sensing unit requires a sensor capable of accurately sensing an amount of water vapor due to high sensitivity to ambient humidity.

Typically, a method for generating photonic crystal and a method for forming nanoparticle structures on the surface of photonic crystal, as well as various devices for detecting various gases and compositions, have been known. However, there is a limit to address the issues, due to the inaccuracy of sensors, sensitivity to humidity, or the like.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide a sensor device configured to accurately identify a volatile compound from water vapor even at high humidity, and a method for manufacturing the sensor device.

Additional aspects will be set forth in part in the description which follows and, in part, will be apparent from the description, or may be learned by practice of the presented embodiments.

In accordance with an aspect of the disclosure, a sensor device is provided. The sensor device includes a measuring transducer including a pixel array on which volatile compounds and water vapor are condensed and a sensitive porous dielectric layer provided in a form of a plurality of spheres constituting the pixel array, a temperature controller provided around the pixel array, and configured to control temperature of each of pixels constituting the pixel array and temperature of the pixel array, a detection device connected to the measuring transducer, and configured to detect a response pattern of the volatile compounds through the pixel array, an analyzer configured to process the response pattern of the volatile compounds, classify the response pattern according to predefined classes by using a predefined machine learning algorithm, and store the response pattern and a classification result corresponding to the response pattern, a stimulating source connected to the measuring transducer, and configured to stimulate the measuring transducer, and a controller connected to the stimulating source, the temperature controller, and the analyzer, and configured to control parameters of the stimulating source and control the temperature of the pixel array by using the temperature controller.

The pixel array may be configured with a plurality of pixels each including two sub-pixels, the two sub-pixels may be provided as a sub-pixel provided as a plurality of hydrophobic spheres and a sub-pixel provided as a plurality of hydrophilic spheres, each of the plurality of hydrophobic spheres may show higher reactivity to the volatile compounds than water vapor by using a coating of a preset material for condensing or adsorbing the volatile compounds in pores of the sensitive porous dielectric layer, corresponding to the respective hydrophobic spheres, and each of the plurality of hydrophilic spheres may show higher reactivity to the water vapor than the volatile compounds.

The plurality of pixels may include a first pixel and a second pixel that is different from the first pixel, and a coating composition of the hydrophobic spheres included in the first pixel may be different from a coating composition of the hydrophobic spheres of the second pixel, and each of gas components of the volatile components may be condensed and adsorbed on the pixel array.

The measuring transducer may be formed based on a photonic crystal structure.

The photonic crystal structure may be provided as at least one of a one-dimensional photonic crystal structure, a two-dimensional photonic crystal structure, or a three-dimensional photonic crystal structure.

The measuring transducer may include a quartz crystal array.

The sensor device according to an embodiment of the disclosure may further include a dielectric substrate provided on the quartz crystal array and including a corresponding sub-pixel of the sensitive porous dielectric layer.

A quartz crystal included in the quartz crystal array may correspond to each sub-pixel.

Quartz crystals provided on one surface of the quartz crystal array may correspond to electrodes provided on the other surface of the quartz crystal array.

A diameter of each of the hydrophobic spheres may range from 20 nm to 500 nm.

A diameter of each of the pores of the sensitive porous dielectric layer may range from 2 nm to 50 nm.

In at least one pixel of the plurality of pixels, a diameter of each of the hydrophobic spheres may be substantially equal to a diameter of each of the hydrophilic spheres.

A diameter of each of hydrophobic and hydrophilic spheres in one pixel of the plurality of pixels may be different from a diameter of each of hydrophobic and hydrophilic spheres in another pixel of the plurality of pixels.

The sensitive porous dielectric layer may be made of silicon dioxide ($SiO_2$).

The sensitive porous dielectric layer may be made of titanium dioxide ($TiO_2$).

The coating of the hydrophobic spheres may be configured with a material including at least one of surface-active materials, silane, silane derivative, alcohol, thiol, carboxylic acid, noble metal nano-particles, or metal oxide.

The sensor device according to an embodiment may further include a sampling unit transferring a sample of a gas mixture from an analyzed volume to the pixel array.

The stimulating source may be provided as a radiation source.

The radiation source may be provided as a laser radiation source.

The radiation source may be provided as a light-emitting diode (LED) or a LED array.

The stimulating source may be provided as a plurality of voltage sources.

The plurality of voltage sources may respectively correspond to quartz crystals provided in the quartz crystal array.

The detection device may be provided as an array of a plurality of detectors, and each of the plurality of detectors may correspond to each of the quartz crystals provided in the quartz crystal array.

The detection device may be provided as a complementary metal-oxide semiconductor (CMOS) array.

The parameters of the stimulating source may be provided as at least one of signal power or frequency.

The pores of the sensitive porous dielectric layer may be formed between two adjacent spheres or when the spheres are in contact with a surface on which the spheres lie.

In accordance with another aspect of the disclosure, a method for manufacturing a sensor device is provided. The method includes forming a sensitive porous dielectric layer overlapping with a measuring transducer associated with a stimulating source, and provided in a form of a plurality of spheres constituting a pixel array provided as a plurality of pixels each including two sub-pixels, setting preset temperature for each of the plurality of pixels by a temperature controller, creating a temperature gradient along an entire surface of the pixel array by the temperature controller, providing a detection device connected to the measuring transducer and configured to detect a response pattern of the volatile compound from the pixel array, providing an analyzer configured to process the response pattern, classify the response pattern according to defined classes by using a preset machine learning algorithm, and store the response pattern and a result of the classification corresponding to the response pattern, and providing a controller connected to the stimulating source, the temperature controller, and the analyzer, and configured to control the parameters of the stimulating source, and control temperature of the pixel array by using the temperature controller.

The forming of the sensitive porous dielectric layer may include forming a plurality of hydrophobic spheres showing higher reactivity to the volatile compounds than water vapor by using a coating of a preset material and a plurality of hydrophilic spheres showing higher reactivity to water vapor than the volatile compounds, wherein the hydrophobic spheres and the hydrophilic spheres respectively correspond to the two sub-pixels.

The method for manufacturing the sensor device, according to an embodiment of the disclosure, may further include selecting a composition of components constituting the coating of the hydrophobic spheres, and setting an adsorption rate of the volatile compounds with respect to surfaces of the hydrophobic spheres and a condensation rate of the volatile compounds in pores of the sensitive porous dielectric layer, determining a size of the hydrophobic and hydrophilic spheres based on a composition of the volatile compounds, and determining and providing a size of a pore of the sensitive porous dielectric layer, the pore formed between the hydrophobic and hydrophilic spheres or when the hydrophobic and hydrophilic spheres are in contact with a surface on which the hydrophobic and hydrophilic spheres lie, based on the size of the hydrophobic spheres and the hydrophilic spheres.

The forming of the sensitive porous dielectric layer may include providing a coating composition of the hydrophobic spheres included in a first pixel included in the plurality of pixels, the coating composition of the hydrophobic spheres being different from a coating composition of the hydrophobic spheres of a second pixel included in the plurality of pixels, and selecting the coating compositions of the hydrophobic spheres included in the first and second pixels according to reactivity to the volatile compounds, wherein each of gas components of the volatile compounds is condensed and adsorbed on the pixel array.

The forming of the sensitive porous dielectric layer may include forming the coating of the hydrophobic spheres by coating the hydrophobic spheres with a material including at least one of surface-active materials, silane, silane derivative, alcohol, thiol, carboxylic acid, noble metal nano-particles, metal oxide, or combinations thereof.

The measuring transducer may be formed based on a photonic crystal structure.

The photonic crystal structure may be provided as at least one of a one-dimensional photonic crystal structure, a two-dimensional photonic crystal structure, or a three-dimensional photonic crystal structure.

The measuring transducer may be provided as a quartz crystal array.

The method for manufacturing the sensor device, according to an embodiment of the disclosure, may further include providing a dielectric substrate provided on the quartz crystal array and including a corresponding sub-pixel of the sensitive porous dielectric layer.

A quartz crystal included in the quartz crystal array may correspond to each sub-pixel.

Quartz crystals provided on one surface of the quartz crystal array may correspond to electrodes provided on the other surface of the quartz crystal array.

A diameter of each of the hydrophobic spheres may be substantially equal to a diameter of each of the hydrophilic spheres.

A diameter of each of hydrophobic and hydrophilic spheres in one pixel of the plurality of pixels may be different from a diameter of each of hydrophobic and hydrophilic spheres in another pixel of the plurality of pixels.

The setting of the preset temperature for each of the plurality of pixels may include reducing, when each of the plurality of pixels is at temperature that is higher than or equal to 0 degrees and lower than or equal to 30 degrees, the temperature of each of the plurality of pixels by 20 to 30 degrees.

The setting of the preset temperature for each of the plurality of pixels may include reducing the temperature by 20 to 30 degrees below operation temperature of the pixel, and the creating of the temperature gradient along the entire surface of the pixel array by the temperature controller may include reducing the temperature by 20 to 30 degrees below the operation temperature of the pixel.

A diameter of each of the hydrophobic spheres may range from 20 nm to 500 nm.

A diameter of each of the pores of the sensitive porous dielectric layer may range from 2 nm to 50 nm.

The sensitive porous dielectric layer may be made of $SiO_2$.

The sensitive porous dielectric layer may be made of $TiO_2$.

A sensor device and a method for manufacturing the sensor device, according to an embodiment of the disclosure, may improve the stability and life of a sensor and accurately identify a volatile compound from water vapor even at high humidity.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which:

FIGS. 2A and 2B are diagrams illustrating ratios of condensed and adsorbed mass with respect to a hydrophobic sub-pixel and a hydrophilic sub-pixel according to various embodiments of the disclosure;

Throughout the drawings, it should be noted that like reference numbers are used to depict the same or similar elements, features, and structures.

DETAILED DESCRIPTION

Figure 1:
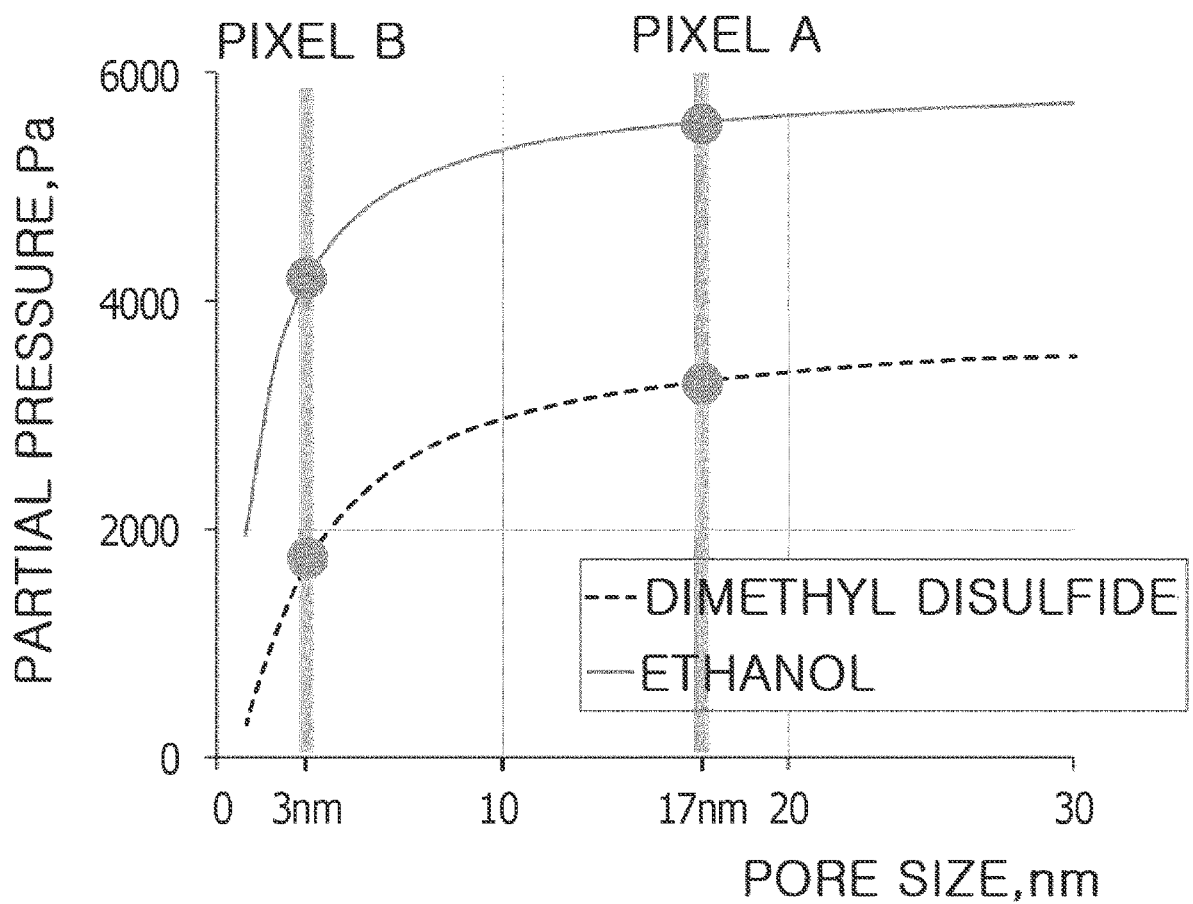
FIG. 1 is a graph illustrating dependence of partial pressure at which a condensation process takes place on pore sizes with respect to two components, that is, dimethyl disulfide and ethanol according to an embodiment of the disclosure.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

A volatile compound sensor device may have a wide range of applications for detecting volatile compounds. Accordingly, volatile compounds should be understood as arbitrary materials being in a gaseous state.

However, before detecting volatile compounds, it may be needed to "train" or "learn" the sensor device with respect to sensitivity to one or another gas composition.

An operation of the volatile compound sensor device on an example of a meat sample in a refrigerator may be considered.

For example, the meat may release dozens of different gases, such as ammonia, methanethiol, trimethylamine, ecetone, dimethyl sulfide, dimethyl disulfide, hydrogen sulfide, or the like.

The gases may enter a sensor configured with a pixel array, wherein each pixel may be configured with a set of spheres made of $SiO_2$, $TiO_2$, or other dielectric materials.

Moreover, because different pixels absorb different amounts of gas, the physical properties of the individual pixels may differ in size of the spheres or chemical coating compositions of the spheres.

For example, spheres made of $SiO_2$ have hydrophilic properties, however, when various compounds/groups are added to modify the surface of the spheres, the properties may change to hydrophobic. Moreover, spheres can be modified to compounds that are specific for a desired gas or gases. For example, modifying a $SiO_2$ surface with gold particles may increase binding of spheres with sulfide gases.

Each pixel will provide an own response, and the pixels of the sensor device (sensor) may together form a specific response pattern. The specific pattern may correspond to rotten meat or fresh meat.

Before a process of recognizing a gas released from a meat sample, a "training" process of the sensor device (sensor) may be performed.

For example, the sensor may be trained or learned with respect to experiment response data of the pixel array, obtained by passing gases released from 100 samples of stale meat having different degrees of freshness through the sensor.

The obtained experiment data may be used to set a machine learning algorithm designed to classify the response data into "latest", "fresh", "later", or "not fresh", in the simplest case. The training results may be uploaded to a controller.

In addition, during a process of detecting quality of a meat sample in a refrigerator, a response result with respect to a volatile compound analyzed from a specific sample may be classified according to a set controller algorithm, and a result of the quality of the meat sample may be displayed based on the response result.

The sensor device may be used to recognize individual volatile compounds, as well as analyzing volatile compounds corresponding to one or another class. For this, it may be needed to "train" the sensor algorithm with respect to the corresponding data samples and assign values to classes of the corresponding volatile compounds.

Thereafter, a process generated in a pixel array will be described below. Gases released from a meat sample may be adsorbed on the surface of spheres forming a porous dielectric layer of the pixel array, and condensed in pores (see FIG. 2C where a pore P is shown) formed when two spheres are connected to each other or spheres are connected to a surface on which the spheres lie. The gases may be adsorbed on the surface of the spheres and condensed in the pores. At the same time, a different amount of released gases may be accumulated on one pixel, according to different conditions.

For example, ratios of accumulated mass may depend on pixels. For example, a specific ratio of amount (mass) may be condensed and adsorbed on a pixel.

For example, when materials of ammonia, dimethyl sulfide, methyl mercaptan, and trimethylamine exist, different pixels may have different ratios of these components.

In addition, different specific responses may correspond to the respective pixels of the array.

One pixel may be not very selective for adsorbed materials, and form a unique pattern together with the other pixels.

A size of a sphere may vary from 20 nm to 500 nm in diameter.

Each pixel may be a combination of two sub-pixels, wherein one of the sub-pixels has hydrophilic properties for predominantly condensing water vapor, and the second sub-pixel has hydrophobic properties for predominantly condensing target volatile components.

As described above, when two adjacent spheres are connected to each other or spheres are connected to a surface on which the spheres lie, pores may be formed. Gases may be adsorbed on the surfaces of the spheres and/or condensed in the pores.

At the same time, a different amount of gases released according to different conditions may be condensed and adsorbed on a pixel. A size of a sphere may vary from 20 nm to 500 nm in diameter. The size of the sphere may decide a size of the pore between the spheres, the size of the pore may decide saturated vapor pressure at which condensation takes place, and the saturated vapor pressure may depend on kinds of gases.

The process may be defined by Equation 1 widely known in the related technical field.

$$IN\frac{P}{P_0} = \frac{2YV_M}{r_c RT}$$ Equation 1

In Equation 1, Y is surface tension, P is saturated vapor pressure in the pore, $P_0$ is saturated vapor pressure above a flat surface, $V_m$ is the molar volume, $R_c$ is the pore size, and R is the gas constant.

Condensation in the pore takes place at lower partial pressure than condensation above the surface or in the volume of air. As described above, the condensation process may depend on the pore size ultimately depending on the size of the spheres.

For example, when a size of a pore P is 3 nm, the size of spheres forming the pore P having the size should be 25 nm to 30 nm. When a size of a micropore is 17 nm, the size of the spheres will be 150 nm to 180 nm.

FIG. 1 is a graph illustrating dependence of partial pressure at which a condensation process takes place on pore sizes with respect to two components, that is, dimethyl disulfide and ethanol according to an embodiment of the disclosure.

Referring to FIG. 1, a graph illustrating the dependence of partial pressure at which a condensation process takes place on pixels A and B having different pore sizes with respect to two components, that is, dimethyl disulfide and ethanol, released from the meat, is considered.

In this case, a dotted line in the graph represents a curve representing condensed dimethyl disulfide, and a solid line represents condensed ethanol. It is seen from the curves that condensation in smaller pores takes place at lower partial pressure than in larger pores.

When the micropore size is 17 nm, ratios of condensed masses of dimethyl disulfide and ethanol may be quite close in value although a difference of about 30% is made.

When the micropore size is 3 nm, a ratio of condensed mass may be about 0.2. By using spheres having different diameters, that is, different pores in the pixel array, selectivity may be controlled.

Each pixel may be a combination of two sub-pixels, wherein one of the sub-pixels has hydrophilic properties for predominantly condensing water vapor, and the second sub-pixel has hydrophobic properties for predominantly condensing mainly a target volatile component.

In this case, the spheres of each pixel of the array may be made of one dielectric material. In addition, the spheres of one pixel may have the same size.

Hydrophobic spheres forming a hydrophobic sub-pixel may be predominantly sensitive to volatile compounds, while sensing water, which may be critical for detection results. For this, the authors of the disclosure have suggested existence in a pixel of a hydrophilic sub-pixel formed from a combination of hydrophilic spheres that are more sensitive to water than other components.

Figure 2B:
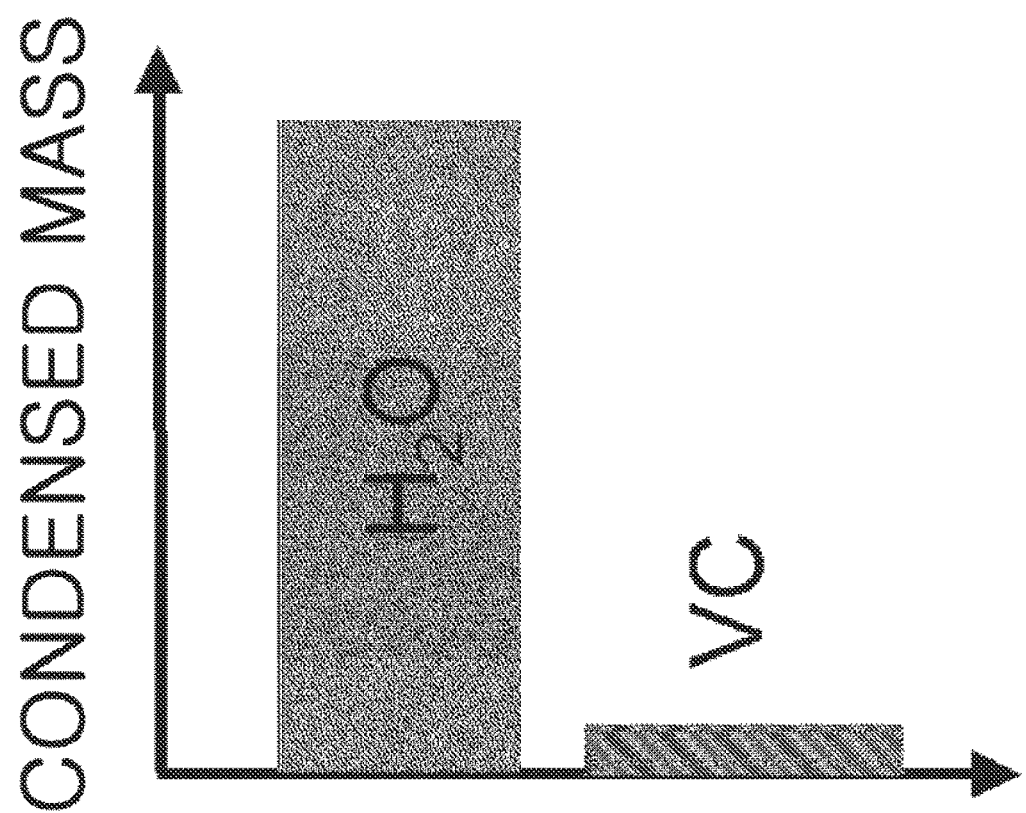

FIGS. 2A and 2B are diagrams illustrating ratios of condensed and adsorbed mass with respect to a hydrophobic sub-pixel and a hydrophilic sub-pixel according to various embodiments of the disclosure.

Figure 2C:
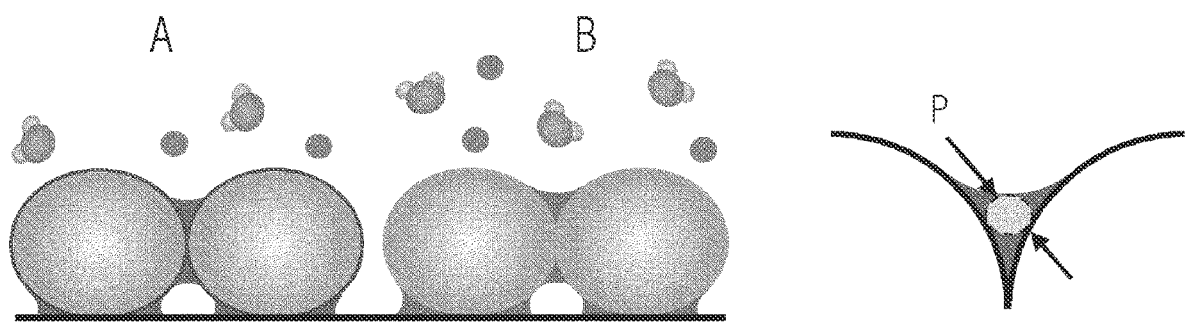
FIG. 2C is a schematic view illustrating pores formed by connecting two spheres to each other or bringing spheres into contact with a surface on which the spheres lie according to an embodiment of the disclosure.

FIG. 2C is a schematic view illustrating pores formed by connecting two spheres to each other or bringing spheres into contact with a surface on which the spheres lie according to an embodiment of the disclosure.

Referring to FIGS. 2A and 2B, ratios of condensed masses with respect to a hydrophobic sub-pixel (FIG. 2A) and a hydrophilic sub-pixel (FIG. 2B) are clearly shown.

Hydrophobic spheres were calibrated in advance in the laboratory, and, when responses to water are known, it was found from laboratory studies that hydrophobic spheres are 200 times more sensitive to water than hydrophilic spheres.

Accordingly, when indicated conditions are known, it may be possible to determine an actual fraction of a response to volatile components VC with respect to each of hydrophobic spheres and hydrophilic spheres from the ratios.

More specifically, the actual fraction P may be determined based on Equation 2.

$$P = S1 - \frac{S2}{200} \quad \text{Equation 2}$$

In Equation 2, P is an actual fraction of a response to volatile components VC, S1 is a signal from hydrophobic spheres, and S2 is a signal from hydrophilic spheres.

At the same time, a difference between the hydrophobic spheres and the hydrophilic spheres may be a coating of the hydrophobic spheres for condensing target volatile components.

The coating of the hydrophobic spheres may be configured with surface-active materials, for example, dimethyl octadecylammonium salt of polyamide acid, polyethylene glycol, stearic, arachidic acid, and their salts.

According to an embodiment of the disclosure, the coating of the hydrophobic spheres may be configured with 3-mercaptopropyltrimethoxysilane, 3-aminopropyltrimethoxysilane, 3-ethoxypropyltrichlorosilane, and silane derivative (trietoxysilane-aminopolyethylene glycol, trimethoxysilane mercaptopolyethylene glycol).

According to another embodiment of the disclosure, the coating of the hydrophobic spheres may be made of at least one material selected from a group including at least one of alcohols including at least one of octanol, decanol, or dodecanol; thiols including at least one of octanethiol, decanthiol, or dodecanthiol; carboxylic acids, for example, butanoic acid, octanoic acid, decan acid, oleic acid; or noble metal nano-particles, for example, gold, silver, or metal oxides, for example, iron or cobalt oxide, or a combination thereof.

Silane derivatives may include compounds configured with an ether silane group (triethoxysilane-, trimethoxysilane group), a linker, and a functional group.

The linker may include hydrophobic materials including polyethylene glycol having various lengths, including hydrocarbon linkers (profile, octyl, decile, or the like).

Meanwhile, a third part of the compounds may include a functional group in which at least one of a thio group, an amino group, a carboxyl group, or an ether group exists.

The authors of the disclosure have conducted studies on the sensitivity of the claimed volatile compound sensor depending on other parameters of the pixel array of the sensor, as well as the coating composition of the pixel array.

In the pixel array of the claimed sensor, some non-limiting examples of pixel implementation will be described below.

First Embodiment

According to an embodiment of the disclosure, a pixel A may be configured with two sub-pixels, wherein one of the sub-pixels is hydrophilic and is represented as a layer of $SiO_2$ spheres, and the other hydrophobic one is represented as a layer of $SiO_2$ spheres modified by gold nano-particles.

According to an embodiment of the disclosure, a size of a sphere may be 20 nm, and a size of a pore between the spheres may be 2 nm.

Temperature maintained at the pixel A may be 20° C. According to an embodiment of the disclosure, gases containing mercapto-, thio-, dithio-, sulfide-, and disulfide-groups may be adsorbed on the pixel.

By using a hydrophobic sub-pixel and a hydrophilic sub-pixel together, the effect of adsorbed water on the hydrophobic sub-pixel may be more clearly separated from adsorbed volatile compounds containing the mercapto-, thio-, dithio-, sulfide-, and disulfide-groups.

Second Embodiment

According to another embodiment of the disclosure, a pixel B may be configured with two sub-pixels, wherein one of the sub-pixels is hydrophilic and is represented as a layer of $SiO_2$ spheres, and the other hydrophobic one is represented as a layer of $SiO_2$ spheres modified by silver nano-particles.

A size of each sphere may be 500 nm, and a size of a pore between the spheres may be 50 nm or smaller. Temperature maintained at the pixel B may be 20° C. By using a hydrophobic sub-pixel and a hydrophilic sub-pixel together, the effect of adsorbed water on the hydrophobic sub-pixel may be separated from adsorbed beneficial volatile compounds.

Adsorption may be characteristic of gases containing mercapto-, thio-, dithio-, sulfide-, and disulfide-groups, however, gases having different ratios in the above-described embodiment may be adsorbed separately because saturated vapor pressure at which condensation takes place depends on the pore size.

Accordingly, a change in pore size by a fixed modification of $SiO_2$ spheres may lead to a change in sensitivity of the pixel to adsorbed gases, which may lead to an increase of information content obtained from the data sensor, which influences an improvement of "training" of the sensor, resulting in a reduction of the number of errors in recognizing volatile compounds.

By using a hydrophobic sub-pixel and a hydrophilic sub-pixel together, the effect of adsorbed water existing in an environment on the hydrophobic sub-pixel may be separated from adsorbed beneficial volatile compounds existing in the environment, thereby enabling a more accurate measurement of target volatile compounds.

Third Embodiment

According to another embodiment of the disclosure, a pixel C may be configured with two sub-pixels, wherein one of the sub-pixels is hydrophilic and is represented as a layer of $SiO_2$ spheres, and the other hydrophobic one is represented as a layer of $SiO_2$ spheres modified by silver nano-particles. A size of a sphere may be 200 nm. A size of a sweat sphere may be 20 nm or smaller. Temperature maintained at the pixel B may be 20° C. By using a hydrophobic sub-pixel and a hydrophilic sub-pixel together, the effect of adsorbed water on the hydrophobic sub-pixel may be separated from adsorbed beneficial volatile compounds.

Adsorption may be characteristic of gases containing mercapto-, thio-, dithio-, sulfide-, and disulfide-groups, however, it will be characterized that gases having a ratio that is different from those in the first and second embodiments are adsorbed because saturated vapor pressure at which condensation takes place depends on the pore size (see Equation 1).

As in the previous embodiments of the disclosure, information content obtained from the sensor may increase by a change of the pore size. By using a hydrophobic sub-pixel and a hydrophilic sub-pixel together, the effect of adsorbed water existing in an environment on the hydrophobic sub-pixel may be separated from adsorbed beneficial volatile compounds existing in the environment, thereby enabling a more accurate identification of target volatile compounds.

Fourth Embodiment

A pixel D may be configured with two sub-pixels, wherein one of the sub-pixels is hydrophilic and is represented as a layer of $SiO_2$ spheres, and the other hydrophobic one is hydrophobic by a layer of $SiO_2$ spheres modified by silver nano-particles. A size of a sphere may be 200 nm. The pore size of the spheres may be set to 20 nm or smaller. Temperature maintained at the pixel B may be 0° C. By using a hydrophobic sub-pixel and a hydrophilic sub-pixel together, the effect of adsorbed water on the hydrophobic sub-pixel may be separated from adsorbed beneficial volatile compounds.

Adsorption may be characteristic of gases containing mercapto-, thio-, dithio-, sulfide-, and disulfide-groups, however, gases having a ratio that is different from those on the above-described pixels A, B, and C may be adsorbed because saturated vapor pressure at which condensation takes place depends on temperature. Accordingly, changes in pore size and temperature of the sensitive layer by a fixed modification of $SiO_2$ spheres may lead to a change in sensitivity of the pixel to adsorbed gases.

This may lead to an increase of information content obtained from the data sensor, which influences an improvement of "training" of the sensor, resulting in a reduction of the number of errors in recognizing volatile compounds. By using a hydrophobic sub-pixel and a hydrophilic sub-pixel together, the effect of adsorbed water existing in an environment on the hydrophobic sub-pixel may be separated from adsorbed beneficial volatile compounds existing in the environment, thereby enabling a more accurate measurement of target volatile compounds.

Fifth Embodiment

A pixel E may be configured with two sub-pixels, wherein one of the sub-pixels is hydrophilic and is represented as a layer of $SiO_2$ spheres, and the other one is hydrophobic by a layer of $SiO_2$ spheres modified by iron oxide nano-particles. A size of a sphere may be 100 nm. The pore size of the spheres may be 10 nm or smaller. Temperature maintained at the pixel C may be 20° C.

Gases containing mercapto-, thio-, dithio-, sulfide-, and disulfide-groups may be adsorbed on the pixel E. Meanwhile, a change in modification of $SiO_2$ spheres may lead to a change in sensitivity of the pixel to adsorbed gases, which may lead to an increase of information content obtained from the data sensor, which influences an improvement of "training" of the sensor, resulting in a reduction of the number of errors in recognizing volatile compounds.

By using a hydrophobic sub-pixel and a hydrophilic sub-pixel together, the effect of adsorbed water existing in an environment on the hydrophobic sub-pixel may be separated from adsorbed beneficial volatile compounds existing in the environment, thereby enabling a more accurate identification of target volatile compounds.

A pixel F may be configured with two sub-pixels, wherein one of the sub-pixels is hydrophilic and is represented as a layer of $SiO_2$ spheres, and the other hydrophobic one is represented by a layer of $SiO_2$ spheres modified by cobalt nano-particles. A size of a sphere may be 300 nm. The pore size of the spheres may be ~30 nm. Temperature maintained at the pixel F may be 20° C.

By using a hydrophobic sub-pixel and a hydrophilic sub-pixel together, the effect of adsorbed water on the hydrophobic sub-pixel may be separated from adsorbed beneficial volatile compounds.

Gases containing mercapto-, thio-, dithio-, sulfide-, and disulfide-groups may be adsorbed on the pixel F.

According to another embodiment of the disclosure, a pixel G may be configured with two sub-pixels, wherein one of the sub-pixels is hydrophilic and is represented as a layer of $SiO_2$ spheres, and the other hydrophobic one is represented by a plurality of $SiO_2$ spheres modified by polyarginine. A size of a sphere may be 260 nm. The pore size of the spheres may be 26 nm. Temperature maintained at the pixel F may be 30° C.

Gases containing an amino group (methylamine, ethyl amine, or the like) may be efficiently adsorbed on the surface of polyarginine. Such a change in modification of the $SiO_2$ spheres may lead to adsorption of other volatile compounds, which may lead to an increase of information content obtained from the data sensor, which influences an improvement of "training" of the sensor, resulting in a reduction of the number of errors in recognizing volatile compounds. By using a hydrophobic sub-pixel and a hydrophilic sub-pixel together, the effect of adsorbed water existing in an environment on the hydrophobic sub-pixel may be separated from adsorbed beneficial volatile compounds existing in the environment, thereby enabling a more accurate identification of target volatile compounds.

Through a series of experiments, the authors of the disclosure found that the layer (plurality) of $SiO_2$ spheres can be modified by any surfactants including amphiphilic polymers, which can be called as hydrophobic polymers. An example of such kinds of materials is polyarginine that effectively absorbs gases containing the amino group. When the above-mentioned hydrophobic polymers are used, the adsorption process will be characteristic of hydrocarbons: hexane, octane, or the like, as well as derivatives containing long hydrocarbon fragments—hexanol, mercaptohexane, or the like.

The authors of the disclosure revealed that the plurality of $SiO_2$ spheres can be modified with various silanes by conducting a series of experiments. Accordingly, for example, gases containing the carboxyl group (acid, ester, or the like) will be efficiently absorbed in the surface of amino silane, and, when hydrophobic silane is used, adsorption may primarily be characteristic of hydrocarbons: hexane, octane, or the like, as well as derivatives containing long hydrocarbon fragments—hexanol, mercaptohexane, or the like.

Modification with alcohols, thiols, and carboxyl acids having various linkers may also be possible. Linkers may be hydrophobic (for example, hydrocarbon), hydrophilic (proteins, polyethylene glycols, or the like), mixed (for example, combining hydrocarbon and fragments' polyethylene glycols (PEGs)), as well as functional groups (thio, amino, carboxy, ether, or the like) at the end of the linker.

It should be noted that the claimed volatile compound sensor is sensitive to a wide range of volatile compounds, and gases released from meat samples, such as ammonia, methanethiol, trimethylamine, acetoin, dimethyl sulfide, dimethyl disulfide, and hydrogen sulfide, are presented in the form of an example that does not limit the entire list of volatile compounds.

The process of condensation and adsorption of volatile compounds released from a meat sample may be controlled by applying different temperatures to the different pixels of the array.

Figure 3A:
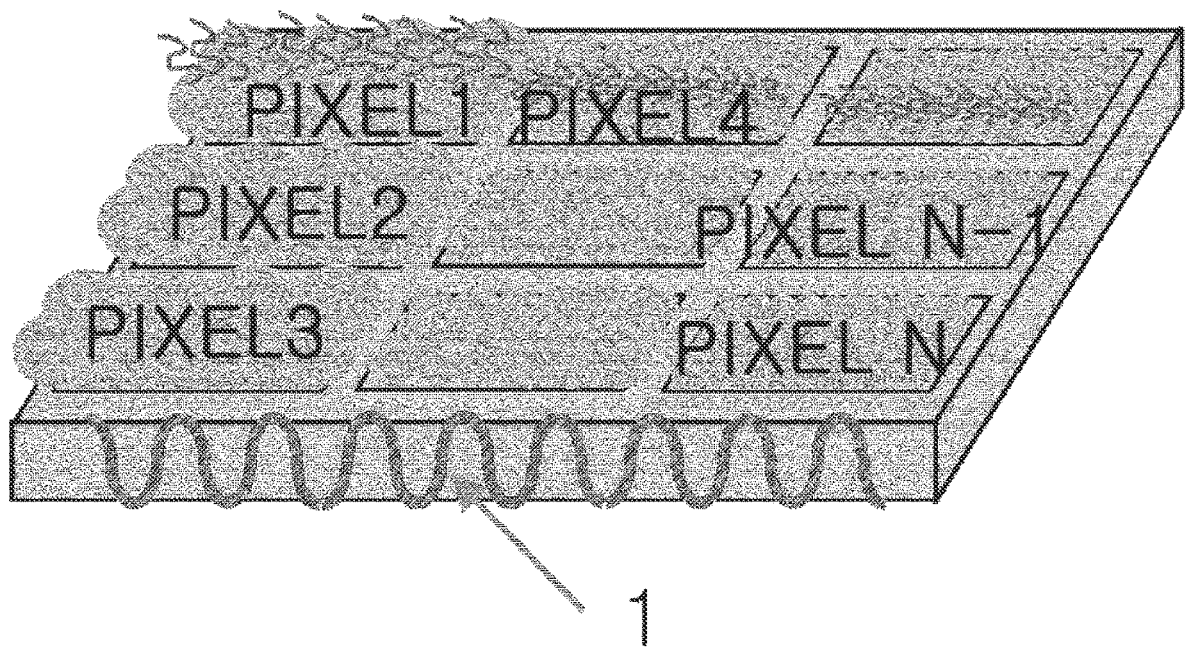
FIG. 3A is a schematic view illustrating a temperature control for each pixel of an array according to an embodiment of the disclosure.

FIG. 3A is a schematic view illustrating a temperature control for each pixel of an array according to an embodiment of the disclosure.

Figure 3B:
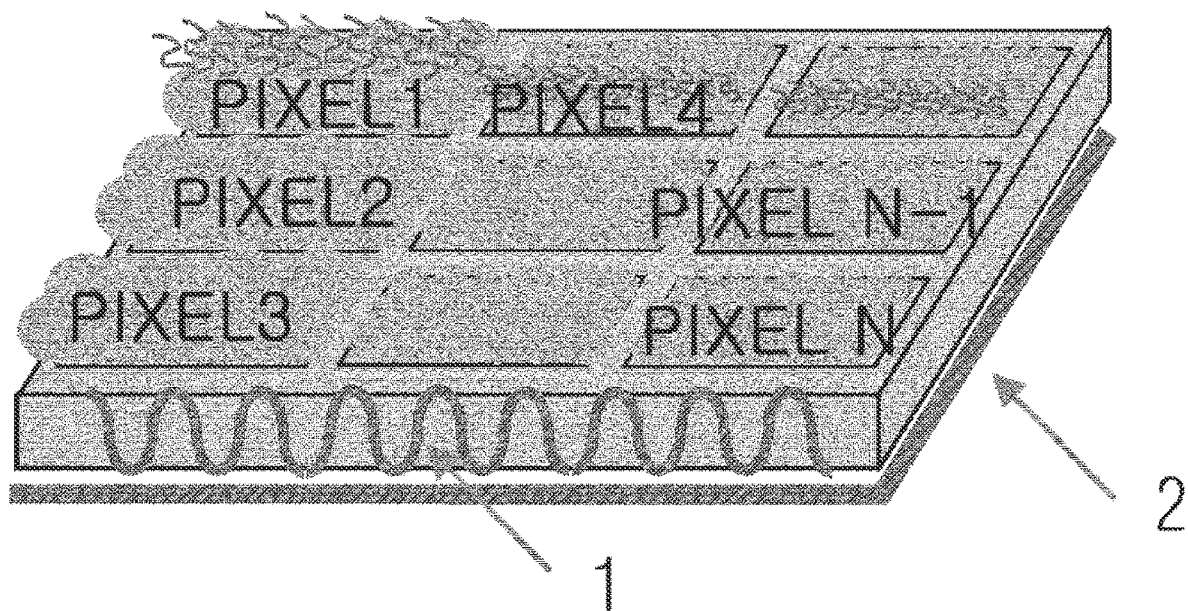
FIG. 3B is a schematic view illustrating a temperature control of an entire array as a whole according to an embodiment of the disclosure.

FIG. 3B is a schematic view illustrating a temperature control of an entire array as a whole according to an embodiment of the disclosure.

Referring to FIGS. 3A and 3B, the process may be carried out by means of a temperature controller which can be used as, for example, a Peltier module 1 or an electric heater 2 through which a temperature gradient is created along the surface of the pixel array and different temperatures can be applied to the entire surface of the array. Thus, the authors of the disclosure provide selective condensation depending on temperature and the ability to control the sensitivity of the entire volatile compound sensor (detection unit).

Figure 4:
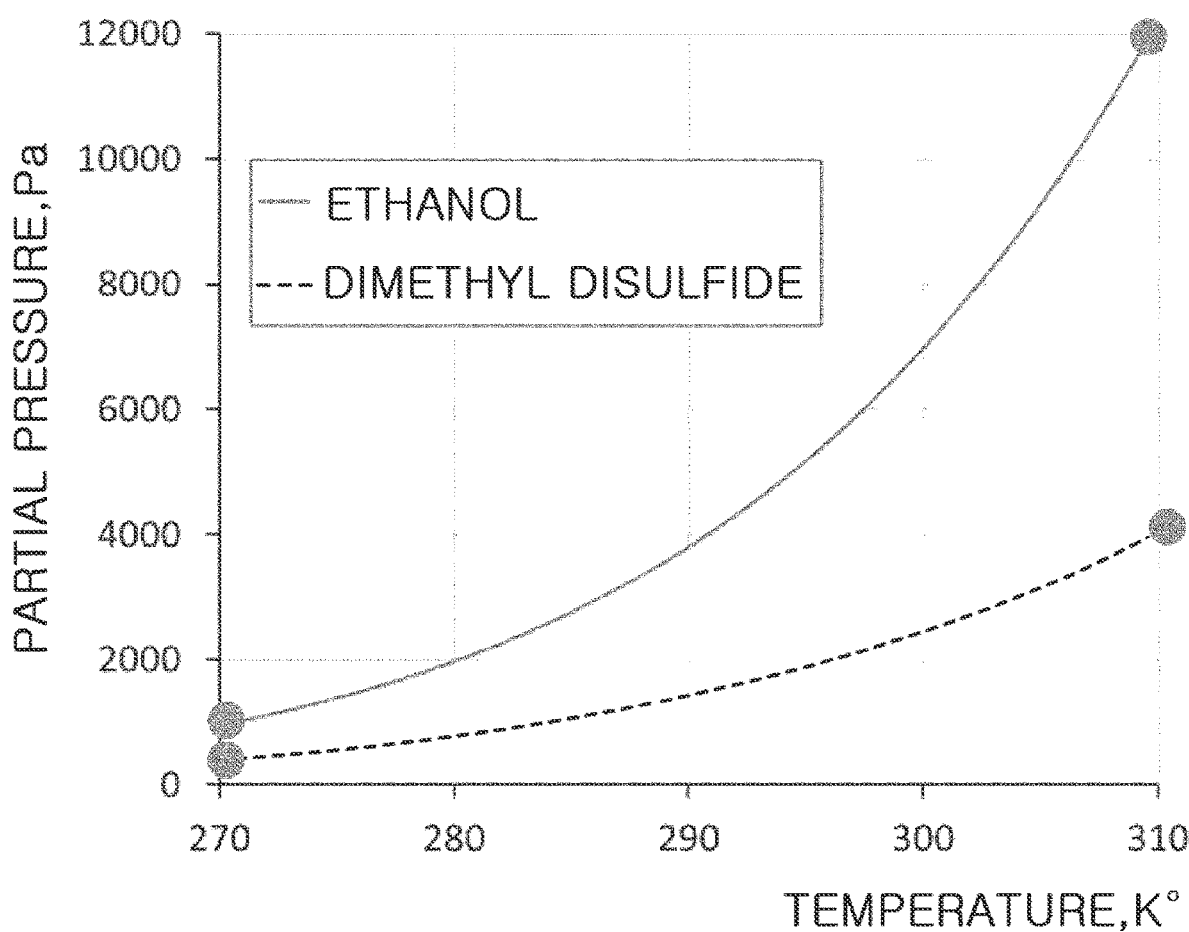
FIG. 4 is a graph illustrating temperature dependence of partial pressure on temperature at which a condensation process takes place with respect to two components, that is, dimethyl disulfide and ethanol, released from meat according to an embodiment of the disclosure.

FIG. 4 is a graph illustrating dependence of saturated vapor pressure on temperature at which the condensation process takes place with respect to two components released from meat, which are dimethyl disulfide and ethanol, for a pixel with pores having a size of 5 nm according to an embodiment of the disclosure.

Referring to FIG. 4, a dotted line in the graph is a curve illustrating condensed dimethyl disulfide, and a solid line is condensed ethanol. It can be seen from the presented curves that the condensation process depends on temperature. As the temperature increases, the fraction of the condensed standard decreases with respect to dimethyl disulfide. In addition, as the temperature increases, condensed mass of each of the components of dimethyl disulfide and ethanol decreases.

Figure 5:
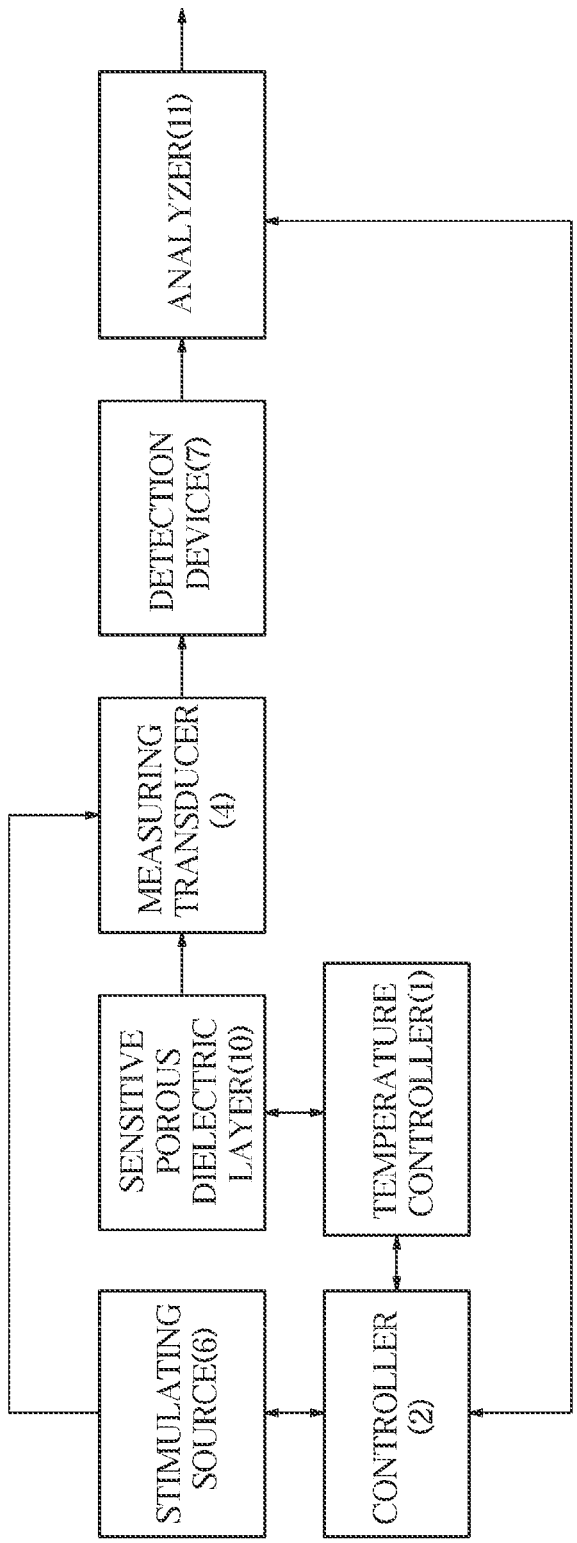
FIG. 5 is a block diagram of a volatile compound sensor device according to an embodiment of the disclosure.

FIG. 5 is a block diagram of a volatile compound sensor device according to an embodiment of the disclosure.

Referring to FIG. 5, when a stimulating source 6 is initiated, a resonance may arise in a measuring transducer 4 made based on an array of photonic crystal or quartz crystals.

A temperature controller 1 may serve to stabilize and control temperature of a sensitive porous dielectric layer 10.

A controller 2 may serve to control parameters of the stimulating source 6, such as signal power and frequency, as well as to control temperature for the temperature controller 1.

In this case, a process of adsorption of volatile compounds on the surface of the spheres, forming the sensitive porous dielectric layer 10, and condensation in pores formed by these spheres, may be initiated, which increases mass of the porous layer and changes a refractive index and thereby leads to a resonance shift in the measuring transducer 4. The shift may be further observed on a detection device 7.

In this case, each sensitive porous dielectric layer 10 will give a response on the detection device 7, the pixels of the sensor device may together form a specific response pattern, which is digitized and transmitted to an analyzer 11, which is a microprocessor or a processor for processing and classifying a received response pattern by using a machine learning algorithm set in advance according to operation results of detection results of studied volatile compounds or detection results of samples, for example, products releasing the volatile compounds.

Figure 6:
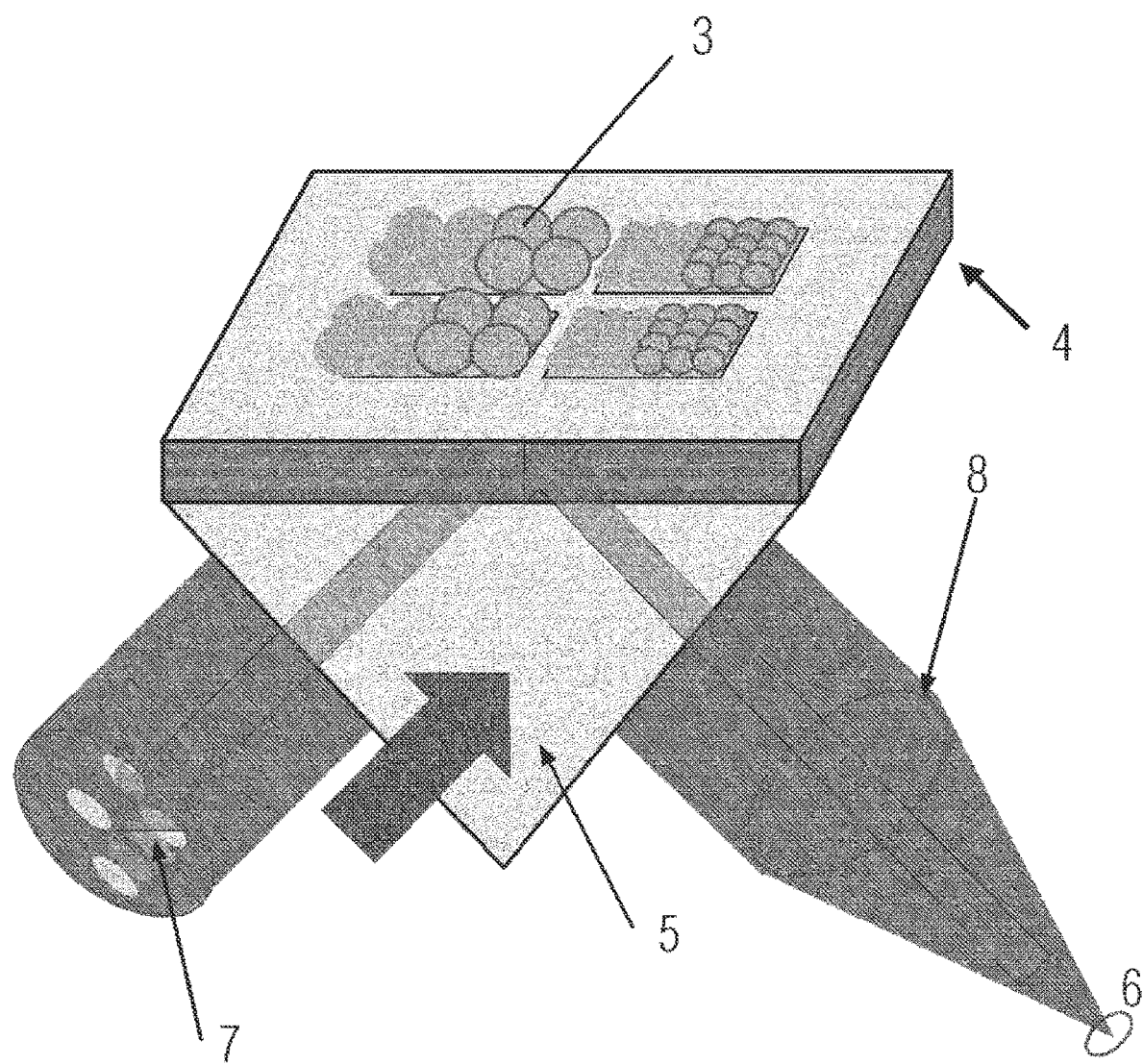
FIG. 6 is a schematic view of a volatile compound sensor device based on photonic crystal according to an embodiment of the disclosure.

FIG. 6 is a schematic view of a volatile compound sensor device based on photonic crystal according to an embodiment of the disclosure.

Referring to FIG. 6, a position reference 3 is a pixel array based on a sensitive porous dielectric layer, and position reference 4 is a measuring transducer in the form of a photonic crystal structure (photonic crystal), specifically, one-dimensional photonic crystal, which is an alternation of a thin dielectric layer with a thickness of 100 nm to 400 nm. Position reference 5 may be a prism, although the position reference 5 can be a waveguide or an optical fiber, position reference 6 may be a stimulating source which is a radiation source, and position reference 7 may be a detection device, for example, a photosensitive array in the form of a CMOS sensor or any other type of detector according to an embodiment of the disclosure.

A beam released from the radiation source 6 may be collimated using an optical collimator 8 and then enter the photonic crystal structure 4, at a certain angle, while illuminating all the pixels of the pixel array 3 with the prism 5. Radiation may be reflected from the surface of the photonic crystal structure 4, again pass through the prism 5, and enter the detection device 7 as a CMOS array.

The radiation may fall on the photonic crystal structure 4 in a given range of angles, while, for the photonic crystal structure 4, there may be an angle at which radiation energy is transferred to the sensitive layer (porous dielectric layer) consisting of spheres in the form of the pixel array 3 with a distance up to 500 nm. The angle can be seen on the detection device 7 as a decrease in incident optical power. Moreover, each pixel on the photonic crystal structure 4 may correspond to a certain region on the detection device 7.

In the process of adsorption and condensation, a change may occur in the refractive index of the sensitive porous dielectric layer formed by the spheres of the pixel array 3, that is, a change in mass of a material condensed on the spheres may lead to a shift of the minimum optical power to a lower angle on the detection device 7.

A response of the volatile compound sensor device can be observed either as a shift of the minimum optical power on the CMOS array (in the case in which the dependence on the angles is measured), or as a change in the intensity of a reflected signal (in the case in which the angle is fixed). In this case, each pixel of the pixel array 3 will give an own response on the detection device 7, the pixels of the volatile compound sensor device may together form a specific response pattern, which is digitized and transmitted to the analyzer where the received response pattern is processed and classified by using a preset machine learning algorithm, and, according to the operation result, for example, a detection result about the quality of studied volatile compounds or samples of a product releasing the volatile compounds may be outputted.

Figure 7A:
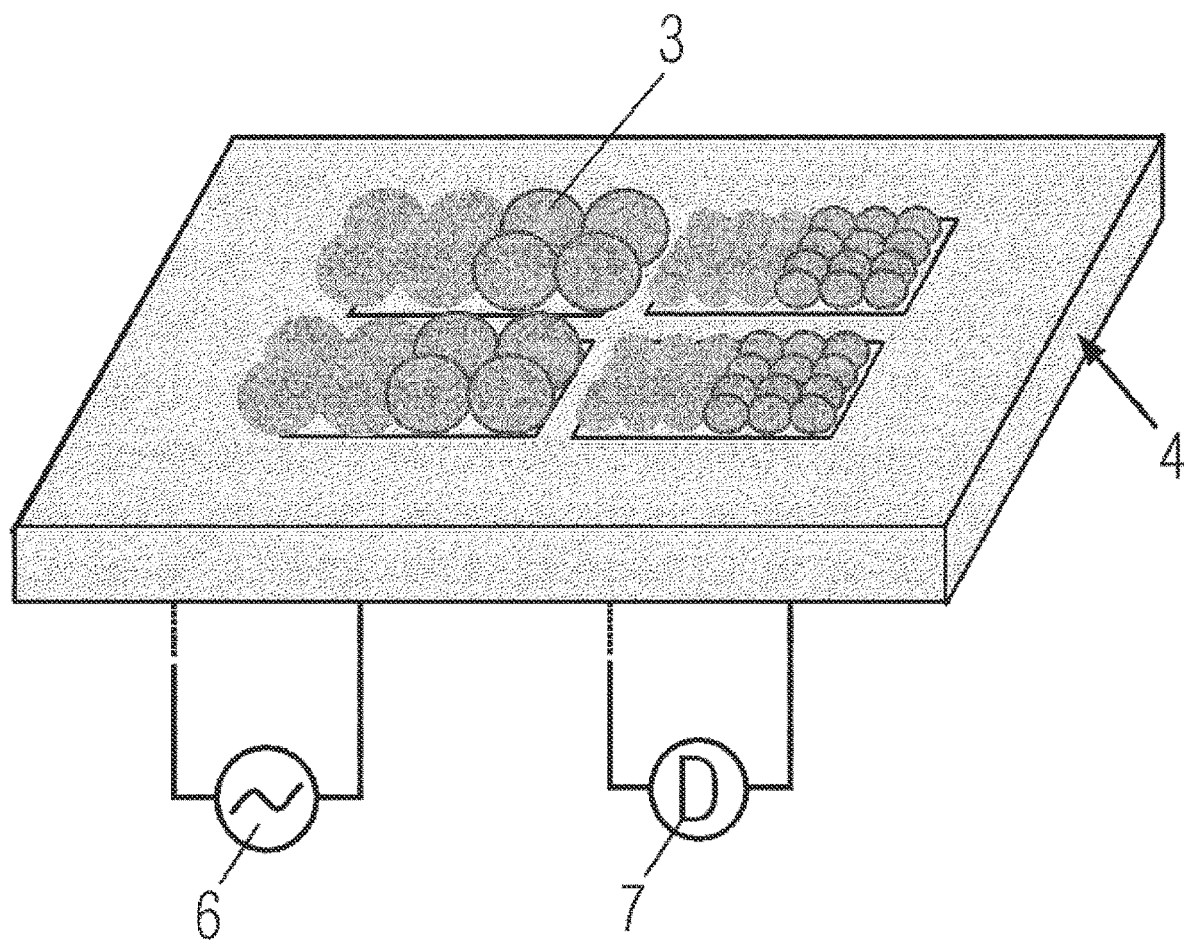
FIGS. 7A, 7B, and 7C are schematic views of a structure of a quartz crystal as a whole for hydrophobic and hydrophobic sub-pixels of pixels A and B, respectively according to various embodiments of the disclosure.
Figure 7B:
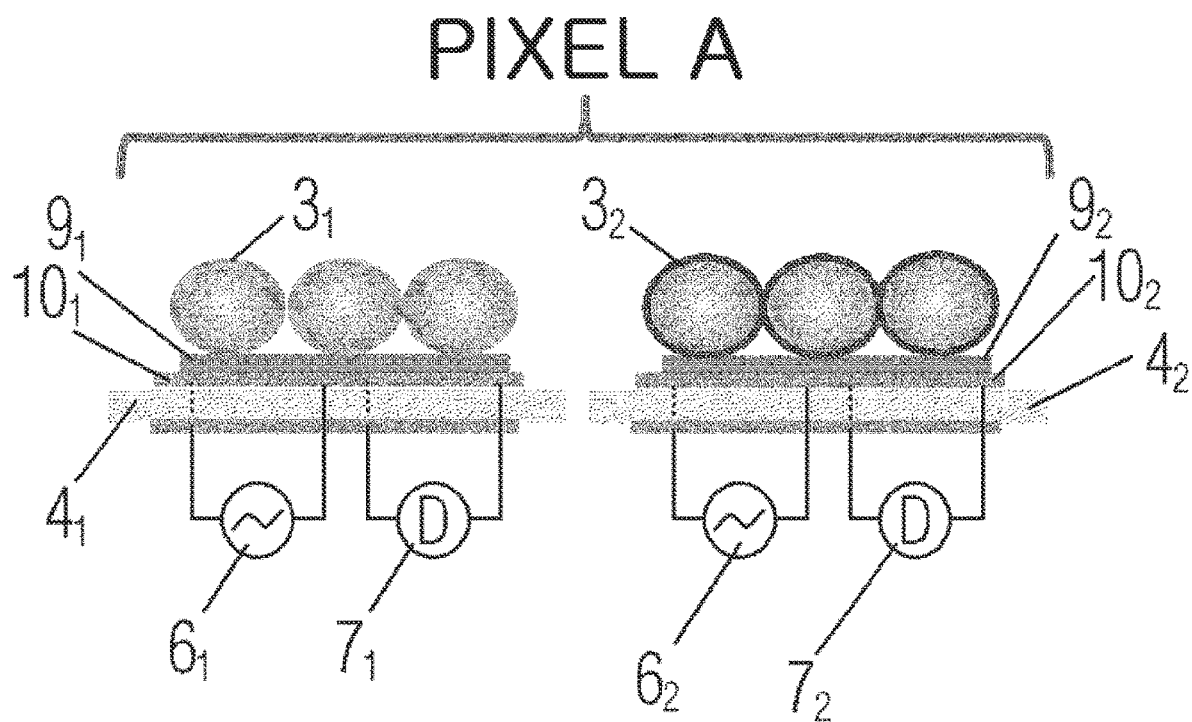
Figure 7C:
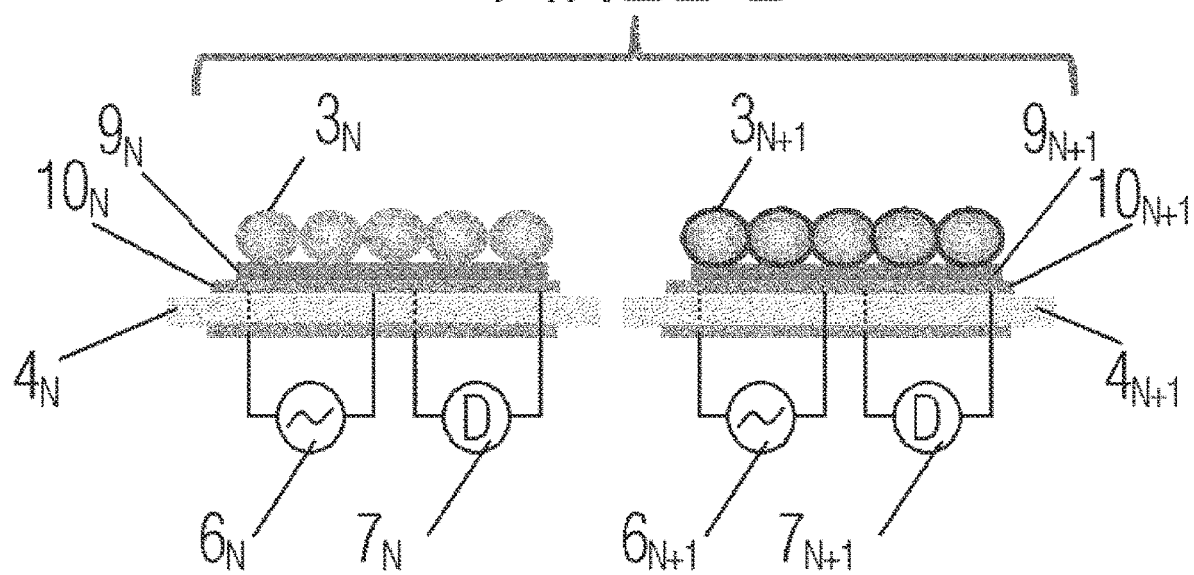

FIGS. 7A, 7B, and 7C are schematic views of a structure of a quartz crystal as a whole for hydrophobic and hydrophobic sub-pixels of pixels A and B, respectively according to various embodiments of the disclosure.

Referring to FIG. 7A, it is a schematic view of a volatile compound sensor device based on an array of quartz crystals, where reference numeral 3 is a pixel array based on a sensitive porous dielectric layer, reference numeral 4 is a measuring transducer in the form of an array of quartz crystals, reference numeral 6 is a stimulating source which is an array of voltage sources containing a plurality of voltage sources, and reference numeral 7 is a detection device, for example, a detector array from a plurality of detectors.

FIG. 7B shows a part of a sensor device for pixel A, and FIG. 7C is for pixel B.

Referring to FIG. 7B, reference numeral $3_1$ is a layer (plurality) of spheres forming a hydrophilic sub-pixel and reference numeral $3_2$ is a layer of spheres forming a hydrophobic pixel of a pixel A located on substrates $9_1$ and $9_2$, respectively. The substrates may be made of a dielectric material. Reference numerals $4_1$ and $4_2$ are quartz crystals of an array of quartz crystals 4, located between plates of electrodes $10_1$ and plates of electrodes $10_2$, respectively.

Referring to FIG. 7C, reference numeral $3_N$ denotes a layer of spheres forming a hydrophilic sub-pixel and reference numeral $3_{N+1}$ denotes a layer of spheres forming a hydrophobic pixel of a pixel B located on substrates $9_N$ and $9_{N+1}$, respectively. The substrates may be made of a dielectric material. Reference numerals $4_N$ and $4_{N+1}$ are quartz crystals of the quartz crystals array 4 located between plates of the electrodes $10_N$ and $10_{N+1}$, respectively. Moreover, each sub-pixel in the array pixel may correspond to a corresponding quartz crystal.

Under action of a voltage supplied by the stimulating source 6, which is a plurality of voltage sources $6_1$ to $6_{N+1}$, electric resonance at crystal natural frequencies may arise in each quartz crystal of the quartz crystals array 4 (measuring transducer).

Moreover, for each quartz crystal, the corresponding voltage source may be provided from the plurality of voltage sources $6_1$ to $6_{N+1}$. The mechanical stress created by the sensitive porous dielectric layer on the quartz crystals, when a voltage is applied to the quartz crystals array, may shift the resonance to a position corresponding to zero. Adsorption of volatile compounds on the surface of the spheres forming the sensitive porous dielectric layer and condensation in the pores formed by these spheres may increase the mass of the porous layer and thereby increase the mechanical stress created by the sensitive porous dielectric layer on quartz crystals, which may lead to an additional shift in the electrical resonance of crystals. The shift may be further observed on the detection device 7 consisting of detectors $7_1$ to $7_{N+1}$, respectively.

In this case, each pixel of the pixel array 3 will give an own response on the detection device 7, the pixels of the sensor may together form a specific response pattern, which may be digitized and transmitted to the analyzer, based on a microprocessor, a processor, or any computing device with a capacity sufficient to perform the following algorithm: classifying response patterns from the test samples of the volatile compounds according to predefined classes using the preset machine learning algorithms, as well as storing the obtained patterns and the results of the classification.

According to an embodiment of the disclosure, adsorption properties of the sensitive porous dielectric material and the sensor for classification into two classes: fresh meat and not fresh meat, can be controlled by fixing mechanisms of a chemical composition of the surface of the material.

Surface energy of the spheres constructing the sensitive porous dielectric material may be changed by various chemical groups, and the property of the interaction of the surface of the spheres with various organic compounds can be hydrogen bonds, Van der Waltz, or dipole interactions.

In addition to regulating the adsorption process on the surface of the spheres constituting the pixel array and condensation in the pores of the sensor, it is possible to measure the rate of the adsorption process on the surface of the spheres depending on the material included in the spheres, thereby increasing the selectivity of the sensor. A signal on the volatile compound sensor may be proportional to an amount of an adsorbed material. The signal may be measured according to time. Therefore, the time derivative of the signal may be the rate of adsorption. Since different materials can have different physical properties of adsorption, the different materials may have different adsorption rates accordingly.

Figure 8:
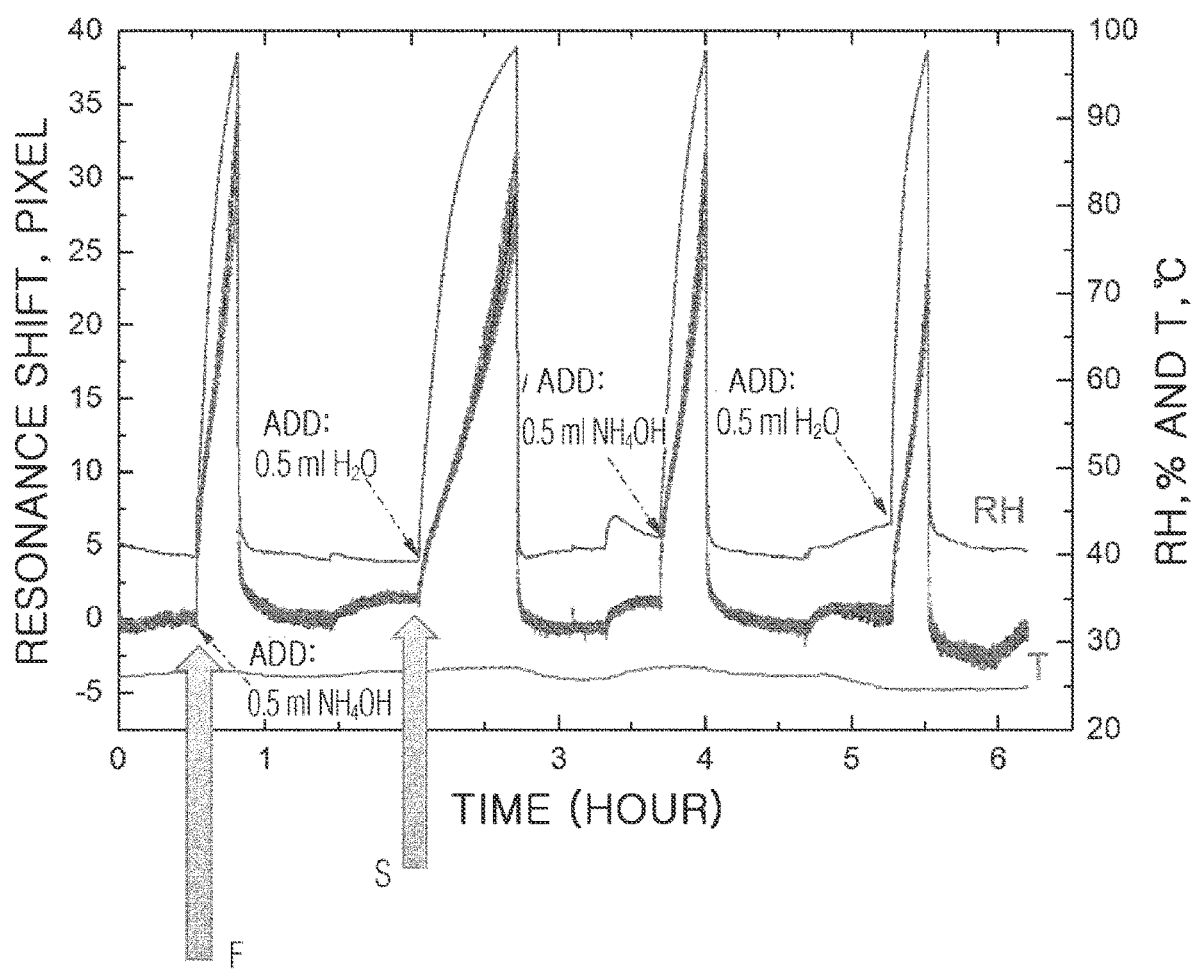
FIG. 8 is a graph illustrating possibility of measuring an adsorption process rate to materials added to a coating of spheres according to an embodiment of the disclosure.

FIG. 8 is a graph illustrating possibility of measuring an adsorption process rate depending on materials added to the coating of the spheres device according to an embodiment of the disclosure.

Referring to FIG. 8, a response of the sensor is presented on one ordinate axis as a resonance shift by the number of array pixels and on the other ordinate axis is relative humidity (RH %) and temperature (T C°), depending on the time (hours) indicated on the abscissa axis. An arrow F in the graph shows that when 0.5 ml of ammonium hydroxide ($NH_4OH$) is added to a container connected to the sensor device, the response of the sensor device is faster, and when 0.5 ml of $H_2O$ (arrow S) is added, the response of the sensor device is slower.

One of the advantages of the claimed sensor device with a reusable function may be the ability to reset the state, which may be achieved by increasing temperature applied to the pixel array 3. When the temperature is increased, evaporation of the whole material from the spheres and the pores and the following purging may be ensured. These actions may reset the state of the sensor to the initial one and the sensor may be renewable, which may be one of the advantages of the present sensor, as mentioned above.

Studies conducted by the authors of the disclosure have shown that in order to clean the sensor device according to the disclosure, it is sufficient to purge the sensor with clean air. In addition, the sensor may be cleaned by increasing temperature. The higher the temperature, the closer the sensor will be restored to an original state, for example, heating of the sensor by 20 to 30 degrees above the operating temperature can be used.

Although the disclosure has been described in connection with some illustrative embodiments of the disclosure, it should be understood that the disclosure is not limited to these specific embodiments. On the contrary, it is assumed that the disclosure includes all alternatives, corrections and equivalents that may be included in the essence and scope of the claims.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. A sensor device comprising:
a measuring transducer including a pixel array on which volatile compounds and water vapor are condensed and a sensitive porous dielectric layer provided in a form of a plurality of spheres constituting the pixel array;
a temperature controller provided around the pixel array, and configured to control temperature of each of pixels constituting the pixel array and temperature of the pixel array;
a detection device connected to the measuring transducer, and configured to detect a response pattern of the volatile compounds through the pixel array;
an analyzer configured to:
process the response pattern of the volatile compounds, classify the response pattern according to predefined classes by using a predefined machine learning algorithm, and
store the response pattern and a classification result corresponding to the response pattern;
a stimulating source connected to the measuring transducer, and configured to stimulate the measuring transducer; and
at least one processor connected to the stimulating source, the temperature controller, and the analyzer, and configured to control parameters of the stimulating source and control the temperature of the pixel array by using the temperature controller,
wherein the pixel array is configured with a plurality of pixels each including two sub-pixels,
wherein the two sub-pixels are provided as a sub-pixel provided as a plurality of hydrophobic spheres and a sub-pixel provided as a plurality of hydrophilic spheres,
wherein each of the plurality of hydrophobic spheres shows higher reactivity to the volatile compounds than water vapor by using a coating of a preset material for condensing or adsorbing the volatile compounds in pores of the sensitive porous dielectric layer, corresponding to the respective hydrophobic spheres, and
wherein each of the plurality of hydrophilic spheres shows higher reactivity to the water vapor than the volatile compounds.

2. The sensor device of claim 1,
wherein the plurality of pixels comprise a first pixel and a second pixel that is different from the first pixel, and
wherein a coating composition of the hydrophobic spheres included in the first pixel is different from a coating composition of the hydrophobic spheres of the second pixel, and
wherein each of gas components of the volatile compounds is condensed and adsorbed on the pixel array.

3. The sensor device of claim 1, wherein the measuring transducer is formed based on a photonic crystal structure.

4. The sensor device of claim 3, wherein the photonic crystal structure is provided as at least one of a one-dimensional photonic crystal structure, a two-dimensional photonic crystal structure, or a three-dimensional photonic crystal structure.

5. The sensor device of claim 1, wherein the measuring transducer comprises a quartz crystal array.

6. The sensor device of claim 5, further comprising a dielectric substrate provided on the quartz crystal array and including a corresponding sub-pixel of the sensitive porous dielectric layer.

7. The sensor device of claim 5, wherein each of quartz crystals included in the quartz crystal array correspond to each of sub-pixels included in the pixels.

8. The sensor device of claim 6, wherein quartz crystals provided on one surface of the quartz crystal array correspond to electrodes provided on the other surface of the quartz crystal array.

9. The sensor device of claim 1, wherein a diameter of each of the hydrophobic spheres ranges from 20 nm to 500 nm.

10. The sensor device of claim 1, wherein a diameter of each of the pores of the sensitive porous dielectric layer ranges from 2 nm to 50 nm.

11. The sensor device of claim 1, wherein, in at least one pixel of the plurality of pixels, a diameter of each of the hydrophobic spheres is substantially equal to a diameter of each of the hydrophilic spheres.

12. The sensor device of claim 1, wherein a diameter of each of hydrophobic and hydrophilic spheres in one pixel of the plurality of pixels is different from a diameter of each of hydrophobic and hydrophilic spheres in another pixel of the plurality of pixels.

13. The sensor device of claim 1, wherein the sensitive porous dielectric layer is made of silicon dioxide ($SiO_2$).

* * * * *